US009393404B2

(12) United States Patent
Decré et al.

(10) Patent No.: US 9,393,404 B2
(45) Date of Patent: Jul. 19, 2016

(54) FREESTANDING THIN FILM FOR A SYSTEM FOR NEURAL APPLICATIONS

(71) Applicant: Sapiens Steering Brain Stimulation B.V., Eindhoven (NL)

(72) Inventors: Michel Marcel Jose Decré, Eindhoven (NL); Edward Willem Albert Young, Maastricht (NL); Jacobus Adrianus Johanna Maria Deckers, Waalre (NL); Dirk van Pijkeren, Waalre (NL); Ke Wang, Valkenswaard (NL); Vincent Adrianus Henneken, Utrecht (NL)

(73) Assignee: MEDTRONIC BAKKEN RESEARCH CENTER B.V., Maastricht (NL)

( * ) Notice: Subject to any disclaimer, the term of this patent is extended or adjusted under 35 U.S.C. 154(b) by 352 days.

(21) Appl. No.: 13/865,375

(22) Filed: Apr. 18, 2013

(65) Prior Publication Data

US 2013/0282090 A1     Oct. 24, 2013

Related U.S. Application Data

(60) Provisional application No. 61/636,177, filed on Apr. 20, 2012.

(30) Foreign Application Priority Data

Apr. 20, 2012   (EP) .................................. 12164860

(51) Int. Cl.
*A61N 1/00* (2006.01)
*A61N 1/05* (2006.01)
(Continued)

(52) U.S. Cl.
CPC ............ *A61N 1/0551* (2013.01); *A61N 1/0529* (2013.01); *A61N 1/0534* (2013.01); *A61N 1/36125* (2013.01); *A61N 2001/086* (2013.01); *H05K 1/00* (2013.01)

(58) Field of Classification Search
CPC ............. A61N 1/00; A61N 1/02; A61N 1/04; A61N 1/372; A61N 1/375; G02B 5/284; G02B 5/285; G02B 5/288; H05K 1/00; H05K 1/02; H05K 1/0212; H05K 1/0213; H05K 1/0274; H05K 1/0277; H05K 1/028; H05K 1/0283; H05K 1/0284; H05K 1/09; H05K 3/1258; H05K 2201/0332; H05K 2201/0364; H05K 2201/05; H05K 2201/09; H05K 2201/09018
See application file for complete search history.

(56) References Cited

U.S. PATENT DOCUMENTS

| 5,178,957 A * | 1/1993 | Kolpe et al. ................... 428/458 |
| 2007/0123765 A1 | 5/2007 | Hetke et al. |
| 2012/0004715 A1 * | 1/2012 | Ramachandran et al. .... 607/137 |

FOREIGN PATENT DOCUMENTS

| CN | 101583309 A | 11/2009 |
| JP | 2001009798 A | 1/2001 |

(Continued)

OTHER PUBLICATIONS

International Search Report and Written Opinion mailed Jul. 17, 2013 for PCT Patent Application No. PCT/EP2013/058005.

(Continued)

*Primary Examiner* — Christopher D Koharski
*Assistant Examiner* — Elizabeth K So
(74) *Attorney, Agent, or Firm* — Shumaker & Sieffert, P.A.

(57) ABSTRACT

A lead for use in neural stimulation comprises a core section having a proximal end and a distal end. A plurality of electrodes is coupled to the core section proximate the distal end. At least one contact is coupled to the core section proximate the proximal end. At least one thin film is wound around the core section from the proximal end to the distal end and electrically coupling the at least one contact and the plurality of electrodes. The at least one thin film forms a curved substantially planar shape in a relaxed state before being wound around the core section.

26 Claims, 4 Drawing Sheets

(51) Int. Cl.
    *H05K 1/00*     (2006.01)
    *A61N 1/36*     (2006.01)
    *A61N 1/08*     (2006.01)

(56) References Cited

FOREIGN PATENT DOCUMENTS

| | | |
|---|---|---|
| JP | 2002501402 A | 1/2002 |
| JP | 2004167258 A | 6/2004 |
| WO | 2007042999 A2 | 4/2007 |
| WO | 2008101225 A2 | 8/2008 |

OTHER PUBLICATIONS

Maruyama Tomohiro et al: "Realization of freestanding wrinkled thin films with flexible deformability"; Applied Physics Letters, AIP, American Institute of Physics, Melville, NY, US, vol. 98, No. 4, Jan. 26, 2011; pp. 41908-41908.

Notification of Reason for Rejection and translation from counterpart Japanese Application No. 2015-506229, dated Sep. 29, 2015, 17 pp.

English Translation of the Third Office Action, from counterpart Chinese Application No. 201380020779.7, dated Mar. 10, 2016, 10 pp.

\* cited by examiner

FREESTANDING THIN FILM FOR A SYSTEM FOR NEURAL APPLICATIONS

CROSS-REFERENCE TO RELATED APPLICATIONS

This application claims the benefit of EP 12 164 860 and U.S. Provisional Patent Application No. 61/636,177 both filed Apr. 20, 2012, entitled "A freestanding thin film, especially a freestanding thin film for a system for neural applications", and incorporated by reference herein in their entirety.

BACKGROUND OF THE INVENTION

The present invention generally relates to thin films, and in some embodiments, thin films for a system for neural applications, methods of manufacturing of thin films, wafers, lead cores for a lead, leads, probes and systems for neural applications. Implantable neurostimulation devices have been used for the past ten and more years to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, and Tremor. New applications of DBS in the domain of psychiatric disorders like obsessive compulsive disorder or depression are being researched and show promising results. In existing systems, probes carrying electrodes are connected to an implantable pulse generator (IPG).

Future systems will need more, smaller electrodes, in order to better control the delivery of electrical stimulation, because current stimulation causes mild to severe side-effects in about 30% of the patients. Magnetic resonance (MR) safety of these implantable devices is an important issue. MR safety, reduction of the heating of the implant as a result of the electrical field during MR scanning, can be realized by winding of the cable wires on the device. However, the winding substantially increases the length of the cable wiring. The DBS lead can be manufactured by winding a thin film around a core. These thin films are typically produced on a carrier wafer or a plate and released from the wafer or plate after manufacturing. In the case of a DBS lead that is manufactured with winded thin film, the length of the thin film is substantial and can exceed the size of the carrier substrate.

Thin films for implanted DBS systems are typically manufactured on a carrier wafer. In general, silicon carrier substrates of either 6 inch (15.24 cm) or 8 inch (20.32 cm) diameter are used. However, a MR safe DBS system will need a thin film of several tens of centimeters. This length exceeds the diameter of the carrier wafer and a simple straight thin film cannot be made.

A known method to overcome this limitation of the carrier substrate size makes use of a foldable thin film design as described in U.S. Patent Application Publication No. 2007/0123765 A1, which is hereby incorporated by reference in its entirety. The folding method has several disadvantages though. Folding the film severely compromises the mechanical properties of the thin film. Folding forces the thin film into a small radius of curvature and stretches the materials at the outer side of the curvature. Meanwhile the folding strains the materials at the inside of the curvature and can cause the materials in the thin film to crack, break and buckle. Moreover, the manufacturing process of leads, the winding of the thin film around a core, is more complicated. At the position of folding, the winding process must be discontinued. The discontinuity of the thin film folding disrupts the winding process of the film around a core.

It is therefore desirable to improve a thin film, a method of manufacturing of a thin film, a wafer, a lead core for a lead, a lead, a probe and a system for neural applications, especially in that thin films can be provided without folding and which exceed the dimensions of a substrate on which the thin film is manufactured.

BRIEF SUMMARY OF THE INVENTION

In one embodiment, a freestanding thin film is provided, whereby the thin film at least partially forms a planary curved winding, in particular a planary spiral winding, when being outstretched on a substantially flat surface.

The thin film may be a thin film for a system for neural applications, more specifically for brain applications. System for brain applications may be e.g. a system for neuromodulation and/or neurorecording, for instance a deep brain stimulation system. The thin film may be embodied as a thin film strip or thin film band. The width of the thin film strip may be greater than its thickness and significantly smaller than its length.

In one embodiment, the present invention provides a solution to manufacture thin films that exceed the length of the carrier wafer without the need of folding the thin film. The method enables the manufacturing of very long thin films on small carrier wafers. Because there is no need to fold the thin film, a wider range of materials and stacks can be used. The winding process of these long thin films is continuous and therefore eases lead manufacturing.

The thin film may be e.g. at least partially formed like the character "6" or like a "G". That means that the thin film in its outstretch arrangement on a flat surface may form a curve on a plain that winds around a fixed centre point at an increasing distance from this point. The radius of the curved winding of the thin film increases, preferably continuously.

In a preferred embodiment, the length of the thin film is greater than the diameter of a substrate wafer used for producing the thin film. In one embodiment, the length of the thin film is not limited by the diameter of the wafer. Rather, due to the curved winding of the thin film, a conventional wafer such as an 8-inch-wafer (a wafer with a diameter of 20.32 cm) can be used to manufacture a freestanding thin film which length exceeds the diameter of the wafer, namely 20.32 cm, without being folded and accommodate more identical films on one single carrier wafer.

The length of the thin film may be at least 21 cm, more preferably at least 25 cm. Additionally or alternatively, the width of the thin film may be not greater than 1.25 mm, especially not greater than 1 mm.

Moreover, the thin film may comprise at least one metal track, which includes at least partially a noble metal. For instance, it is possible that the at least one metal track comprises at least one section comprising a high conductive metal and a low conductive metal, whereby the low conductive metal is a biocompatible metal and has a lower electrical conductivity than the high conductive metal and whereby the high conductive metal is at least partially encapsuled by the low conductive metal, whereby preferably the high conductive metal comprises gold and/or copper and/or aluminium and/or silver or is gold or copper or aluminium or silver and/or the low conductive metal comprises platinum and/or titanium and/or titanium nitride or is platinum or titanium or titanium nitride.

A low conductive metal (LCM) is a metal with a relatively low electrical conductivity or a metal alloy with a relatively low electrical conductivity, e.g. with an electrical conductivity σ within the range of about $2.00 \times 10^6$ to $9.75 \times 10^6$ S/m, especially between $2.38 \times 10^6$ and $9.43 \times 10^6$ S/m at 20° C. The electrical resistivity ρ of the low conductive metal (LCM) may be within the range of about $1.00 \times 10^{-7}$ to $4.50 \times 10^{-7}$ Ωm at 20° C., especially between $1.06 \times 10^{-7}$ and $4.20 \times 10^{-7}$ Ωm at 20° C.

A high conductive metal (HCM) is a metal with a relatively high electrical conductivity or a metal alloy with a relatively high electrical conductivity, e.g. with an electrical conductivity σ within the range of about $3.00 \times 10^7$ to $7.00 \times 10^7$ S/m, especially between $3.50 \times 10^7$ and $6.30 \times 10^7$ S/m at 20° C. The electrical resistivity ρ may be within the range of about $1.50 \times 10^{-8}$ to $3.00 \times 10^{-8}$ Ωm at 20° C., especially between $1.59 \times 10^{-8}$ and $2.82 \times 10^{-8}$ Ωm at 20° C.

Biocompatible metal in sense of the present invention means e.g. a metal or metal alloy, which has the ability of a biomaterial to perform its desired function with respect to a medical therapy, without eliciting any undesirable local or systemic effects in the recipient or beneficiary of that therapy, but generating the most appropriate beneficial cellular or tissue response in that specific situation, and optimizing the clinically relevant performance of that therapy. In other words, a biocompatible metal in sense of the present invention means e.g. a metal or metal alloy, which is non-toxic to e.g. the brain tissue and/or can be implanted into a human body, preferably into the human brain without or with minor deleterious effects.

In one embodiment, a method of manufacturing a freestanding thin film, especially a freestanding thin film for neural applications, is provided, whereby at least one material to form the thin film is deposited as such that it forms at least partially a planary curved winding, in particular a planary spiral winding, on substantially flat surface after being deposited on said flat surface.

The flat surface may be a wafer like a carrier wafer or a substrate wafer. For instance, the wafer can be a silicon wafer of 6 inch (15.24 cm) diameter or of 8 inch (20.32 cm) diameter.

The deposition of the thin film onto the wafer may be carried out by a chemical vapour deposition (CVD) method or a physical vapour deposition (PVD) method. It is preferred to use a physical vapour deposition method, in particular sputtering. All known types of sputtered deposition processes may be used for depositing the thin film onto the wafer in order to manufacture the freestanding thin film. In particular, ion-beam sputtering, reactive sputtering, ion-assisted deposition, high-target utilization sputtering, high-power pulse magnaton sputtering (hipimis) and our gas flow sputtering may be applied. The thin film deposited onto the substrate may subsequently be released from the substrate by an etching process, for example by dry etching or wet etching. The etching process may remove the substrate and thus release the freestanding thin film.

Additionally, it is possible that on the flat surface at least two or several thin films, in particular thin film strips, are deposited. The thin films or thin film strips, respectively, may be at least partially arranged in parallel on the substantially flat surface. By this, several thin films can be arranged on the same substantially flat surface. Preferably, the flat surface is a surface of a carrier wafer such as a silicon wafer, which may have a substantially rounded shape. The carrier wafer may also be formed as a glass wafer, preferably having a rectangular shape. If the thin films are at least partially formed like the character "6" or like a "G", the spirally wound thin films can be arranged into each other in parallel and thus several identical thin films may be deposited on the surface of e.g. a substrate like a round wafer. In this way, a high amount of thin film strips per single wafer can be produced.

Such thin film may comprise a distal end carrying the electrodes of the thin film and a proximal end comprising the connecting means for a connection to e.g. a connecting wire of an IPG. All distal ends and/or proximal ends can be arranged on merely the same circular line respectively with the same radius with respect to the midpoint, i.e. the center, of the wafer.

In one embodiment, a wafer, especially a carrier wafer, is provided having at least one surface, whereby on the at least one surface at least one thin film is deposited, said thin film at least partially forming a planary curved winding, in particular a planary spiral winding, when being outstretched on the flat or planar surface of the wafer.

In one embodiment, a lead core for a lead, especially for a system for neural applications, is provided, whereby the lead core comprises at least one lead core section which has a shape that is configured such that a freestanding thin film can be laid and/or wound on and/or around this shape, said thin film forming at least partially a planary curved winding, in particular a planary spiral winding, when being outstretched on a substantially flat surface.

Especially, it is possible that the lead core or the at least one lead core section comprises at least one groove for receiving the thin film or, respectively, the thin film strip wherein the groove is configured such that the thin film or thin film strip can be fully embedded within the groove. The groove may also be configured such that the thin film and the lead core form a substantially flat outer surface after being mounted to each other.

It has been turned out that winding of the freestanding thin film around a substantially cylindrical lead core shows a characteristic winding profile. The outer peripheral edge of the thin film sags upon winding around the lead core due to the planar curved winding which the thin film formed during manufacturing on the planar wafer surface. The lead core having a groove for the thin film allows accommodating the sagging of the thin film upon winding. In particular, the groove may be formed such that the thin film, if wound around the lead core and, in particular, arranged inside the groove, contact the groove, especially a base of the groove, holohedrally. Preferably, the groove extends along the lead core in a helical shape, i.e. the groove is helically arranged around the longitudinal axis of the lead core. The groove may further comprise a groove base which is inclined with respect to the longitudinal axis such that the thin film, when mounted on the lead core, and the groove base fully contact each other. This is to ensure that the thin film is well protected and does not form a corrugation on the outer surface of the lead core. Moreover, the groove allows covering the thin film with a protecting layer, e.g. with epoxy glue. The protecting layer may be applied such that only the groove or grooves of the lead core are filled with the protection layer in order to form a smooth outer surface and a good protection for the thin film.

Moreover, it is possible that the lead core is at least partially made of polymer and/or is a stylet and/or that the lead core has a core diameter within a range of about 0.5 mm to about 1.5 mm, especially within a range of about 0.75 mm to about 1.25 mm, whereby preferably the core diameter is about 1 mm.

In one embodiment, a lead, especially a lead for a system for neural applications, is provided.

In one embodiment, the invention relates to a method of manufacturing of a thin film by using a spiral design. This design enables the manufacturing a thin film of which length exceeds the size of the carrier substrate that is used during the manufacturing process.

A further idea relates to a carrier wafer with a spiral design thin film. The thin film may include metal tracks of a noble metal that are encapsulated in insulating Silicon oxide and nitride. A polymer, typically parylene may be used to form a thin film.

Figure 4:
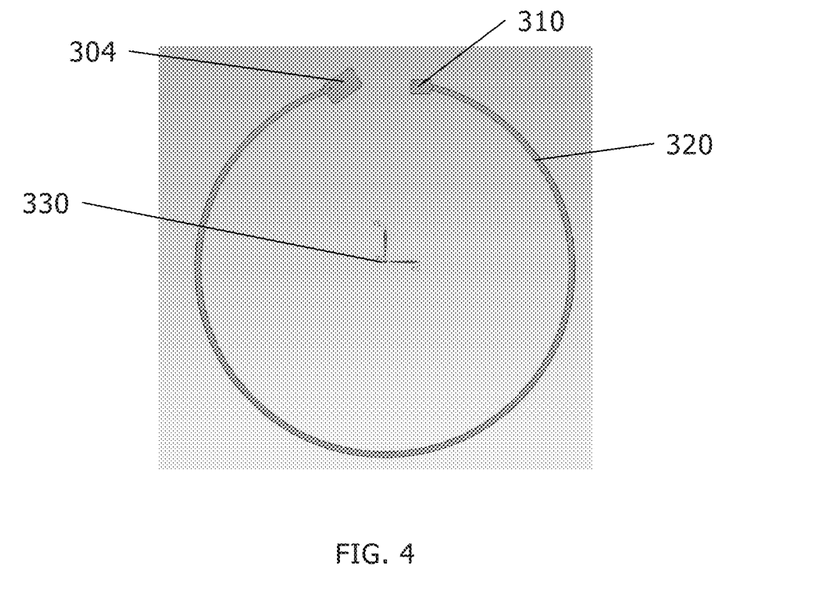
FIG. 4 is a plan view of a freestanding thin film in accordance with an exemplary embodiment of the present invention.

In one embodiment, the invention makes use of a carrier wafer with a parallel spiral design (see FIG. 4). This configuration enables the manufacturing of multiple spiral designed films on a wafer. The manufacturing of multiple thin films or, respectively, electrodes on one wafer reduces the costs of manufacturing. The proposed configuration further enables for all thin films being identical which is essential for production and subsequent lead manufacturing.

In one embodiment, a thin film made on a carrier wafer is provided with a spiraling design to manufacture a thin film that in length exceeds the substrate size (diameter for circular substrates, length or width for square substrates). Spiraling can best be realized by a configuration of parallel spiraling to make sure that all thin films are identical.

In one embodiment, a lead has a thin film manufactured out of a spiraling design on the carrier wafer shows a characteristic winding profile around a core. The outer peripheral shows sagging upon winding around the core. The thin film may have a width of 1 mm as well as the core of the lead (lead core) which also may have a diameter of about 1 mm in cross section. It has developed that average sagging of such a thin film in wound position around the lead core is in the order of one to several tens of microns and depends on the radius of the film, the width of the film and the core diameter. If unwound and positioned back to the flat configuration, as on the carrier wafer, the freestanding thin film will show the original typical spiral form again.

In one embodiment, a lead core is provided with a shape to accommodate the sagging of the thin film upon winding. A groove may be provided for the thin film to make sure that the thin film is well protected and does not form a corrugation on the outer surface of the lead. The groove with the thin film in it can be filled with epoxy glue to form a smooth outer surface and a good protection for the thin film.

In one embodiment, a probe is provided with a lead manufactured with a thin film from a spiraled design.

BRIEF DESCRIPTION OF THE SEVERAL VIEWS OF THE DRAWINGS

The foregoing summary, as well as the following detailed description of embodiments of the freestanding thin film for a system for neural applications, will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

Figure 1:
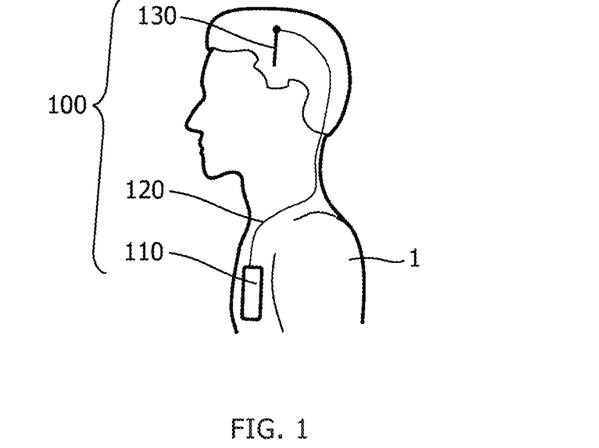
FIG. 1 is a schematic drawing of a neurostimulation system for deep brain stimulation (DBS) in accordance with an exemplary embodiment of the present invention.

A possible embodiment of a neurostimulation system 100 for deep brain stimulation (DBS) is shown in FIG. 1. The neurostimulation system 100 comprises at least a controller 110 that may be surgically implanted in the chest region of a patient 1, typically below the clavicle or in the abdominal region of a patient 1. The controller 110 can be adapted to supply the necessary voltage pulses. The typical DBS system 100 may further include an extension wire 120 connected to the controller 110 and running subcutaneously to the skull, preferably along the neck, where it terminates in a connector. A DBS lead arrangement 130 may be implanted in the brain tissue, e.g. through a burr-hole in the skull.

Figure 2:
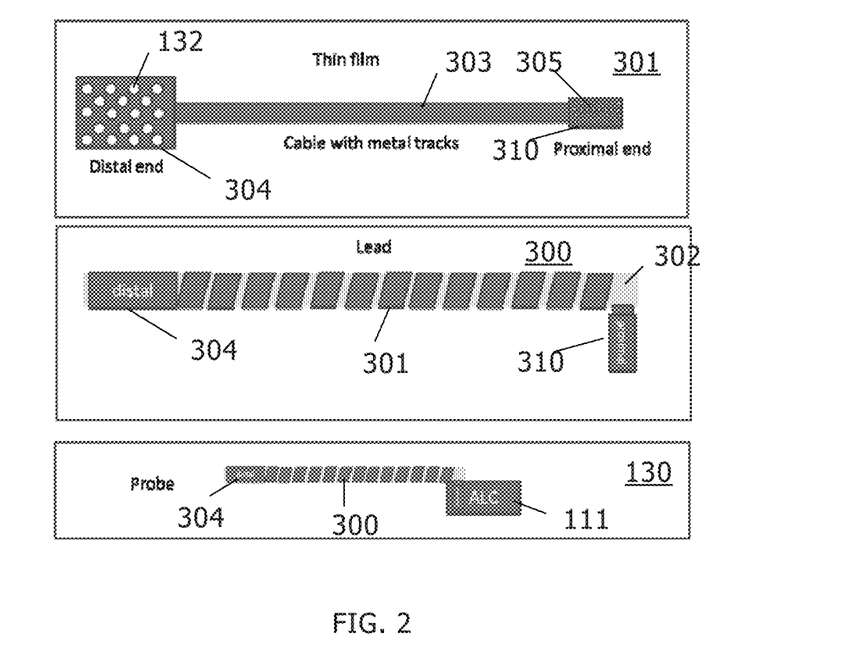
FIG. 2 is a further schematic drawing of a probe neurostimulation system for deep brain stimulation (DBS) and its components in accordance with an exemplary embodiment of the present invention.

FIG. 2 further illustrates a typical architecture for a Deep Brain Stimulation probe 130 that comprises a DBS lead 300 and an Advanced Lead Connector (ALC) element 111 comprising electronic means to address electrodes 132 on the distal end 304 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300. The thin film 301 for a lead is preferably formed by a thin film product having a distal end 304, a cable 303 with metal tracks and a proximal end 310. The proximal end 310 of the thin film 301 on the lead 300 is electrically connected to the ALC element 111. The ALC element 111 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises of metal lines (not shown) to connect each distal electrodes 132 to a designated proximal contact 305.

Figure 3:
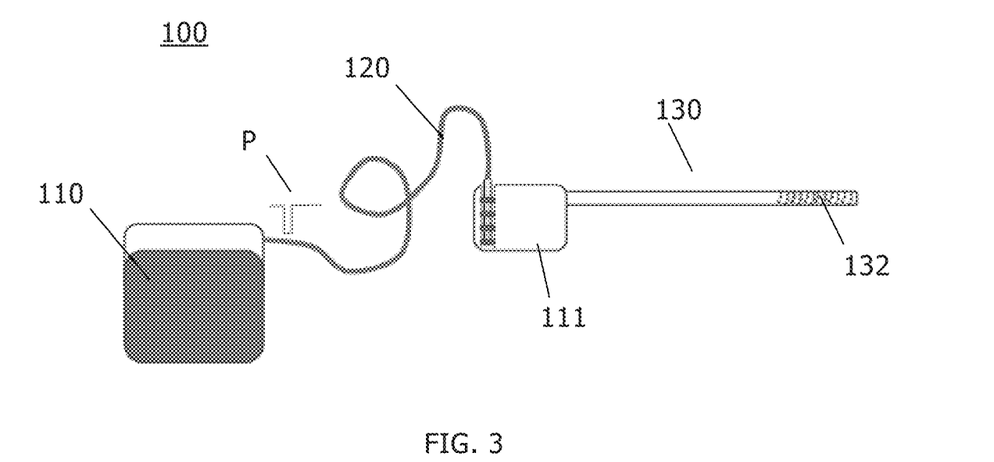
FIG. 3 is a schematic drawing of a probe system in accordance with an exemplary embodiment of the present invention.

FIG. 3 shows schematically and in greater detail an embodiment of a system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, whereby e.g. 64 electrodes 132 can be provided on outer body surface at the distal end of the probe 130. By means of the extension wire 120 pulses P supplied by controller 110 can be transmitted to the ALC 111. The controller 110 can be an implantable pulse generator (IPG) 110.

FIG. 4 shows the general principle of the present invention. The present invention relates to a freestanding thin film 301, in particular a thin film strip 320 or thin film band, having at least one section which is wound in a planary curved shape. The thin film strip 320 of FIG. 4 has a proximal end 310 and a distal end 304. The distal end carries a plurality of electrodes 132, particularly stimulate electrodes. The electrodes are adapted to apply an electric and/or electromagnetic stimulation field within neural tissue, in particular brain tissue. The proximal end 310 includes a connecting element, having a plurality of interconnect contacts 305 corresponding to interconnecting contacts of the ALC. As such, the proximal end 310 of the thin film strip 320 can be connected to the ALC element 111.

As is apparent from FIG. 4, the thin film strip 320 is outstretched on a planar surface and has a curved shape. In one embodiment, outstretched means the original, relaxed and un-tensioned state of the film strip 320. The thin film strip 320 is curved around a center point 330 wherein the radius of the curve formed by the thin film strip 320 varies. Starting from the proximal end 310, the curved thin film strip 320 runs to the distal end 304 with the radius increasing. According to the embodiment of FIG. 4, the thin film strip 320 completely is shaped in a planar curve, in particular a planar spiral. However, the thin film strip 320 may include sections which form a planary curved winding or a planary spiral winding. Other sections may have different shapes or different amounts of curvature. It may be possible that the thin film strip 320 or the thin film 301 in general has at least partially an oval shape or a circular shape.

In order to increase the length of the thin film 301 or the thin film strip 320, it is preferred that the thin film strip 320 forms a planary spiral winding. Thereby, the distal end 304 of the thin film strip 320 may overlap the proximal end 310 and thus the length of the thin film strip 320 may be increased. It is to be noted that the curved or spiral winding of the thin film strip 320 is formed on a common plane such that the distal end 304 and the proximal end 310 of the thin film strip 320 are arranged in that plane. Thus, the distal end 304 of the thin film strip 320 is arranged in a different distance from the center point 330 than the proximal end 310. Preferably, as it is apparent from FIG. 4, the distance between the distal end 304 and the center point 330 is greater than the distance between the proximal end and the center point 330.

Figure 5:
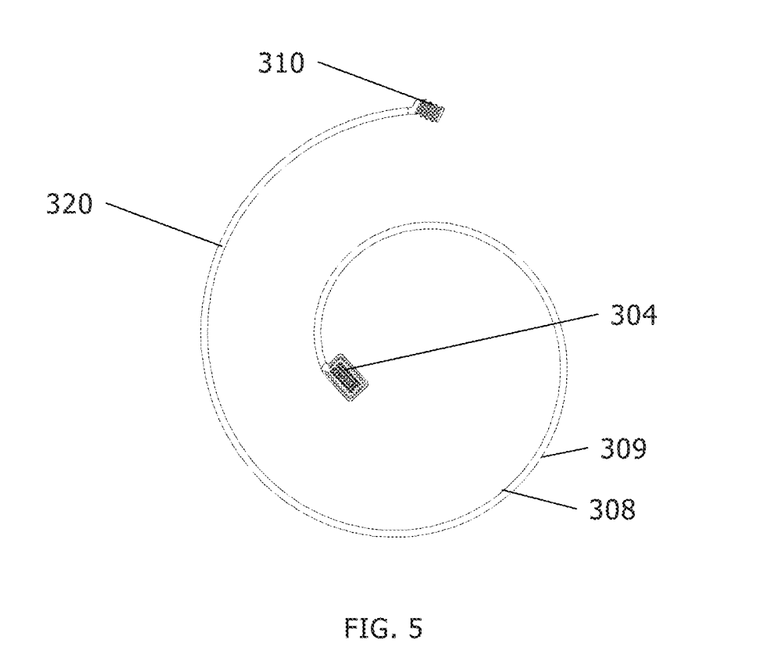
FIG. 5 is a plan view of a freestanding thin film which is spirally wound in a single plane.

FIG. 5 shows a thin film strip 320 wherein the distal end 304 overlaps the proximal end 310. In this case, the distal end 304 is arranged in a distance to the center point 330 (not shown) which is significantly smaller than the distance between the proximal end 310 and the center point 330. As such, the thin film 301 or the strip 320 formed by the thin film 301 is shaped substantially in the form of the letter "G" or the character "6". Due to the difference in distance between the distal end 304 and the center point 330 and the proximal end 310 and the center point 330, a gap exists between the overlapping sections of the thin film strip 320. The advantage of having a relatively large gap between the overlapping sections of the thin film strip 320 is apparent from FIG. 6.

Figure 6:
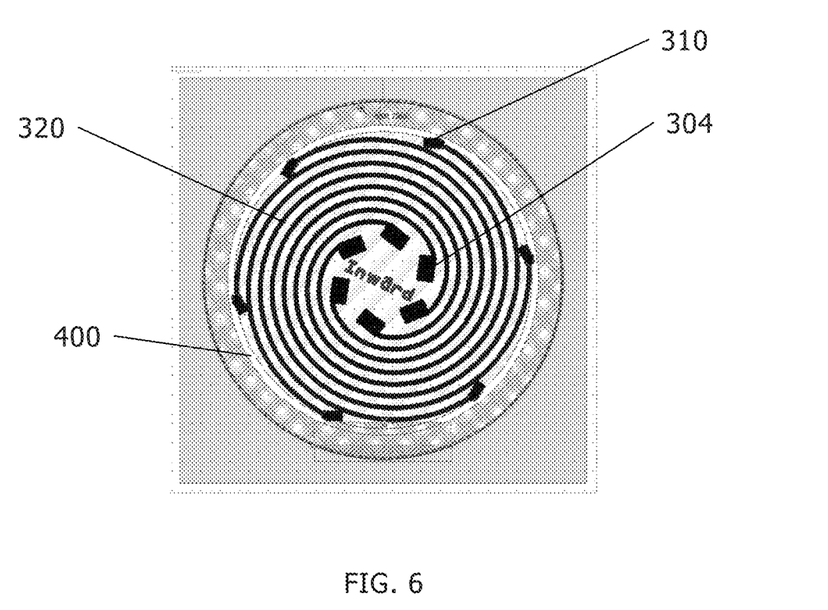
FIG. 6 is a plan view of a round wafer carrying a plurality of deposited thin film strips which are spirally wound in parallel.
Figure 7:
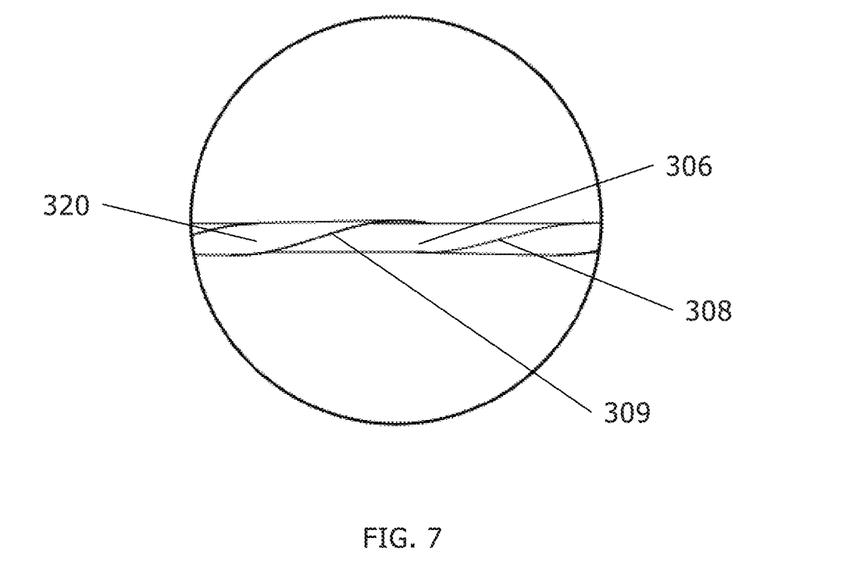
FIG. 7 is a side view of a lead with a freestanding thin film according to the present invention attached thereto.

FIG. 6 shows a plan view of a wafer 400 on which several thin film strips 320 are deposited. The deposition of the thin film 301 for forming a thin film strip 320 may be performed by a sputter deposition process. Following one single thin film strip 320, it is apparent that a relatively large gap exists between the overlapping sections of that thin film strip 320. In particular, each thin film strip 320 runs from the center of the wafer 400 in a curved, particularly spirally curved, shape to the outer periphery of the wafer 400. Thus, the distance between the distal end 304, which is arranged near the center of the wafer 400, and the proximal end 310, which is located near the edge of the wafer 400, corresponds approximately to the radius of the wafer 400. Due to this distance between the overlapping sections of the thin film strip 320, a plurality of thin film strips 320 can be arranged in parallel on the wafer 400. Thus, the surface area, which is used as a substrate for the deposition process, can be efficiently exploited.

FIG. 6 further shows that all distal ends 304 of the thin film strips 320 are arranged on the same circular line which extends around the center point 330 or, respectively, the midpoint of the wafer 400. In other words, the center of the circular line on which the distal ends 304 are arranged, corresponds to the midpoint of the wafer 400. The same applies for the proximal ends 310 which are arranged near the outer periphery or the outer edge of the wafer 400. The proximal ends 310 are also arranged on a circular line which center point corresponds to the midpoint of the wafer 400.

The thin film strip 320 being planary wound on a flat surface has an outer peripheral edge 309 and an inner peripheral edge 308 as illustrated in FIG. 5. Due to the manufacturing of the thin film 301, in particular the thin film strip 320, in a planary curved or spirally wound shape on the wafer 400, the thin film 301 tends to sag when wound around a lead core 306 helically, i.e. in a three dimensional spiral shape. This specially applies to the outer peripheral edge 309 of the thin film strip 320, i.e. the outer peripheral edge 309 has a greater radius than the inner peripheral edge 308 of the thin film strip. The radius of the outer peripheral edge 309 and the inner peripheral edge 308 differs by the width of the thin film strip 320.

The thin film 301 may have a width of 1 mm. The diameter of the lead core 306 preferably may be 1 mm. Depending on the winding radius of the thin film strip 320 in the wound position around the lead core 306, the sagging of the thin film strip 320 is proximately in the order of 10 micrometer. This dimension may vary if the width of the thin film 301 and the diameter of the lead core 306 are different. It goes without saying that if the thin film strip 320 is unwound and positioned back to the flat configuration, i.e. the thin film strip 320 is outstretched on a flat surface, as e.g. on the carrier wafer 400 or the substrate in general, the thin film strip 320 will show the original curved or spiral shape which is typical for the present invention.

Figure 8:
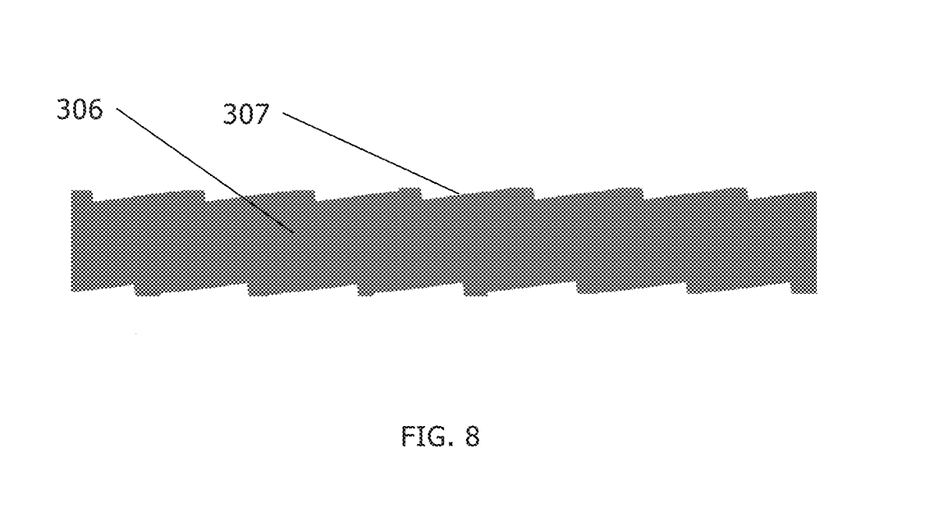
FIG. 8 is a longitudinal section of a lead core adapted to accommodate the sagging of the thin film strip upon winding.

In order to accommodate the sagging of the thin film upon winding, in one embodiment, a lead core 306 has at least one groove 307 which helically extends along the lead core 306. The groove 307 has a width substantially corresponding to the width of the thin film strip 320. The depth of the groove 307 may correspond to the thickness of the thin film strip 320 but preferably is greater than the thickness of the thin film strip 320. As shown in FIG. 8, the groove 307 may have an ascending slope such that the thin film strip 320 fully contacts the outer surface of the lead core 306. Thus, the shape of the lead core 306 takes account of the sagging or twisting of the thin film strip 320.

The groove 307 may be filled with a covering or protecting layer (not shown) after arranging the thin film strip 320 therein. The covering protects the thin film strip 320 and avoids the thin film 301 directly contacting human tissue when implanted. Moreover, the covering may be arranged such that the lead core 306 gets a smooth outer surface. In other words, the groove 307 with the thin film strip 320 arranged therein, may be completely filled with a covering material such that the lead core 306 obtains an outer surface without any unevenness. The covering material may include or be epoxy glue. The covering material, e.g. the epoxy glue, may be applied to the lead core 306 after winding the thin film 301 to the groove 307 so as to fill the groove until a smooth surface of the lead core 306 is achieved.

The method of manufacturing a thin film 301 or a thin film strip 320 for use in e.g. medical applications may comprise the following steps:

In a first step, a carrier wafer 400, preferably consisting of silicon, is provided. The wafer 400 may be sliced from a silicon single crystal. Alternatively, a glass carrier plate can be applied. In a final stage of the thin film 301 manufacturing process, the thin film 301 is released from the carrier wafer 400. Release of the thin film 301 or the thin film strip 320, respectively, may be achieved by removing the substrate, i.e. the silicon wafer, preferably by an etching process.

As stated at the beginning, the length of a thin film 301 manufactured the conventional way cannot exceed the diameter of the carrier wafer 400 and folding of straight thin films 301 is a method to circumvent this size limitation problem. The present invention provides an alternative to solve the size limitation of the carrier wafer 400 on the thin film 301 length. A spiral or at least curved design enables the manufacturing of thin films 301 on a carrier substrate with a length that exceed the diameter of the carrier wafer 400 by far.

In one embodiment, an application of the present invention is in the area of deep brain stimulation (DBS) leads with enhanced magnetic resonance (MR) compatibility. DBS leads can be manufactured with thin films 301. For MR compatibility, a winding of the thin film 301 around a lead core 306 is applied. This leads to the application of thin films 301 or thin film strips 320 with a considerable length. The length exceeds the diameter of the carrier wafer 400. For safety reasons, the metal tracks in the thin film 301 may be sandwiched in inorganic, and preferably biocompatible, materials to ensure electrical insulation for a prolonged period of time. This materials stack is susceptible to mechanical damage due to bending. Thus, the state of the art method of folding the thin film 301 is inapplicable for producing thin film strips 320 with a greater length than allowed by the diameter of the wafer 400. With the method of manufacturing according to the present invention, folding can be avoided. The present invention rather enables the manufacturing of relatively long thin film strips 320 without folding.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

REFERENCE LIST 1 patient
100 neurostimulation system
110 controller
111 advanced lead connector (ALC)
120 extension wire
130 probe
132 electrodes
300 lead
301 thin film
302 carrier
303 cable
304 distal end
305 interconnect contacts
306 lead core
307 groove
308 inner peripheral edge
309 outer peripheral edge
310 proximal end
330 center point
400 wafer

We claim:

1. A freestanding thin film for a system for neural applications, the thin film comprising a curved winding, wherein the curved winding, when laid on a substantially flat surface that defines a surface plane, defines a curved, substantially planar shape in a plane substantially parallel to the surface plane of the substantially flat surface.

2. The thin film according to claim 1, wherein the curved winding comprises a spiral winding.

3. The thin film according to claim 1, wherein a length of the thin film is greater than the diameter of a substrate wafer used for producing the thin film.

4. The thin film according to claim 1, wherein the length of the film is at least 21 cm.

5. The thin film according to claim 1, wherein the length of the film is at least 25 cm.

6. The thin film according to claim 1, wherein the width of the thin film is not greater than 1.25 mm.

7. The thin film according to claim 1, wherein the width of the thin film is not greater than 1 mm.

8. The thin film according to claim 1, wherein the thin film comprises at least one metal track which at least partially comprises a noble metal.

9. The thin film according to claim 8, wherein the at least one metal track comprises at least one section comprising a high conductive metal and a low conductive metal, wherein the low conductive metal is a biocompatible metal and has a lower electrical conductivity than the high conductive metal, and wherein the high conductive metal is at least partially encapsulated by the low conductive metal.

10. The thin film according to claim 9, wherein the high conductive metal comprises at least one of a gold, copper, aluminum, or silver, and the low conductive metal comprises at least one of a platinum, titanium, or titanium nitride.

11. The thin film according to claim 1, wherein the curved shape is substantially in a form of one of a letter "G" or a numerical character "6" in the plane substantially parallel to the surface plane of the substantially flat surface when laid on the substantially flat surface.

12. The thin film according to claim 1, wherein the curved winding includes a distal end and a proximal end, wherein the curved shape is configured such that the distal end is nearer a center point of the curved shape than the proximal end when laid on the substantially flat surface.

13. The thin film according to claim 12, wherein the distal end and proximal end overlap each other and are separated by a gap when laid on the substantially flat surface.

14. The thin film of claim 1, wherein the thin film includes at least one electrode and at least one metal track electrically coupled to the at least one electrode, and wherein the thin film is configured to at least one of deliver electrical stimulation to a patient or sense electrical activity of the patient via the at least one electrode and the at least one metal track.

15. A lead for a system for neural applications, the lead comprising a thin film, the thin film comprising a curved winding, wherein the curved winding, when laid on a substantially flat surface that defines a surface plane, defines a curved, substantially planar shape in a plane substantially parallel to the surface plane of the substantially flat surface.

16. The lead of claim 15, wherein the curved shape is substantially in a form of one of a letter "G" or a numerical character "6" in the plane substantially parallel to the surface plane of the substantially flat surface when laid on the substantially flat surface.

17. The lead of claim 15, wherein the curved winding includes a distal end and a proximal end, and wherein the curved shape is such that the distal end is nearer a center point of the curved shape than the proximal end when laid on the substantially flat surface.

18. The lead of claim 15, further comprising an elongated core, wherein the thin film is wound around the elongated core.

19. The lead of claim 15, wherein the thin film includes at least one electrode and at least one metal track electrically coupled to the at least one electrode, and wherein the lead is configured to at least one of deliver electrical stimulation to a patient or sense electrical activity of the patient via the at least one electrode and the at least one metal track.

20. A probe for a system for neural applications, the probe comprising a thin film, the thin film comprising a curved winding, wherein the curved winding, when laid on a substantially flat surface that defines a surface plane, defines a curved, substantially planar shape in a plane substantially parallel to the surface plane of the substantially flat surface.

21. The probe of claim 20, wherein the curved shape is substantially in a form of one of a letter "G" or a numerical character "6" in the plane substantially parallel to the surface plane of the substantially flat surface when laid on the substantially flat surface.

22. The probe of claim 20, wherein the curved winding includes a distal end and a proximal end, wherein the curved shape is such that the distal end is nearer a center point of the curved shape than the proximal end when laid on the substantially flat surface.

23. The probe of claim 20, further comprising an elongated core, wherein the thin film is wound around the elongated core.

24. The probe of claim 20, wherein the thin film includes at least one electrode and at least one metal track electrically coupled to the at least one electrode, and wherein the probe is configured to at least one of deliver electrical stimulation to a patient or sense electrical activity of the patient via the at least one electrode and the at least one metal track.

25. A medical device system comprising:
   a lead comprising a thin film, the thin film including a curved winding, wherein the curved winding, when laid on a substantially flat surface that defines a surface plane, defines a curved, substantially planar shape in a plane substantially parallel to the surface plane of the substantially flat surface; and
   an implantable medical device coupled to the lead, wherein the implantable medical device is configured to at least one of deliver electrical stimulation to a patient or sense electrical activity of the patient via the lead.

26. The system of claim 25, wherein the thin film includes at least one electrode and at least one metal track electrically coupled to the at least one electrode, and wherein the implantable medical device is configured to at least one of deliver the electrical stimulation to the patient or sense the electrical activity of the patient via the at least one electrode and the at least one metal track.

* * * * *